United States Patent
Reid et al.

(10) Patent No.: US 6,613,549 B2
(45) Date of Patent: Sep. 2, 2003

(54) PROBIOTIC THERAPY FOR NEWBORNS

(75) Inventors: Gregor Reid, London (CA); Andrew W. Bruce, Toronto (CA); Victor Han, London (CA)

(73) Assignee: Urex Biotech, Inc., London (CA)

( * ) Notice: Subject to any disclaimer, the term of this patent is extended or adjusted under 35 U.S.C. 154(b) by 51 days.

(21) Appl. No.: 09/780,841

(22) Filed: Feb. 9, 2001

(65) Prior Publication Data

US 2001/0036453 A1 Nov. 1, 2001

Related U.S. Application Data

(60) Provisional application No. 60/181,702, filed on Feb. 10, 2000.

(51) Int. Cl.[7] .............................................. C12N 1/20
(52) U.S. Cl. ............................. 435/93.45; 424/93.44; 424/93.46; 424/93.51; 435/252.9; 435/252.1; 435/253.4; 435/254.21
(58) Field of Search ...................... 424/93.45, 93.44, 424/93.46, 93.51; 435/252.9, 252.5, 253.4, 254.21

(56) References Cited

U.S. PATENT DOCUMENTS

| | | | |
|---|---|---|---|
| 3,984,575 A | * 10/1976 | Farr | .............. 424/93.45 |
| 5,902,578 A | 5/1999 | Halpin-Dohnalek et al. | |
| 5,922,375 A | 7/1999 | Luchansky et al. | |
| 6,132,710 A | * 10/2000 | Panigrahi et al. | .............. 424/93.45 |

FOREIGN PATENT DOCUMENTS

| | | |
|---|---|---|
| WO | WO 95/33046 | 12/1995 |
| WO | WO 00/71138 | 11/2000 |

OTHER PUBLICATIONS

SU 1 743 607 (1992), Mosc Second Med Inst., Abstract.

Mackie, R. et al., "Developmental microbial ecology of the neonatal gastrointestinal tract", *Am J. Clin Nutr*, 69: 1035S–1045S (1999).

Dai, D. et al., "Protective Nutrients and Bacterial Colonization in the Immature Human Gut", *Advances in Pediatrics*, 46: 353–382 (1999).

Shornikova, A. et al., "Bacteriotherapy with *Lactobacillus reuteri* in rotavirus gastroenteritis", *The Pediatric Infectious Disease Journal*, 16(12): 1103–1107 (1997).

Millar, M. et al., "Enteral feeding of premature infants with *Lactobacillus GG*", *Archives of Disease in Childhood*, 69: 483–487 (1993).

Shornikova, A. et al., "*Lactobacillus reuteri* as a Therapeutic Agent in Acute Diarrhea in Young Children", *Journal of Pediatric Gastroenterology and Nutrition*, 24:399–404 (1997).

Griffin, C. et al., "Feeding preterm infants after hospital discharge: effect of dietary manipulation on nutrient intake and growth", *Pediatr Res*, 43(3):355–60 (1998).

Caplan, M. et al., "Neonatal Necrotizing Enterocolitis: Possible Role of Probiotic Supplementation", *Journal of Pediatric Gastroenterology and Nutrition*, 30:518–522 (2000).

Saxelin, M. "*Lactobacillus GG*—A Human Probiotic Strain with Thorough Clinical Documentation", *Food Rev. Int.*, 13(2):293–313 (1997).

* cited by examiner

*Primary Examiner*—Irene Marx
(74) *Attorney, Agent, or Firm*—Scully, Scott, Murphy & Presser

(57) ABSTRACT

The invention relates to probiotic microbes, including but not limited to Lactobacillus species and Bifidobacteria species, and their compositions and methods of employing said compositions for treating and preventing intestinal and other infections which originate from the intestine, in newborn infants. The invention also invention relates to the ability of probiotic organisms, either in viable or nonviable state, or their by-products, to interfere with pathogenic infection through short and long term colonization of the intestine, inhibition of growth of the pathogens, and assisting the host to fight off the infecting organisms.

5 Claims, No Drawings

PROBIOTIC THERAPY FOR NEWBORNS

CROSS-REFERENCE TO RELATED APPLICATION

This application claims priority from U.S. Provisional Application No. 60/181,702, filed Feb. 10, 2000.

FIELD OF THE INVENTION

The present invention relates to compositions and methods employing probiotic microbial compositions for treating and preventing intestinal and other infections which originate from the intestine, in newborn infants.

BACKGROUND OF THE INVENTION

Each year, intestinal infections kill more people in the world than any other disease. Many of the victims of intestinal infections are children in Third World Countries. The causative agents are mainly bacteria and viruses. Presuming the availability and access to antibiotics and other chemotherapeutic treatments (and many in the Third World do not have such access), these intestinal and urogenital infections are usually not fatal. However, increased antibiotic resistance and poor nutrition and hygiene result in continually elevated morbidity and mortality rates.

Once a child is born, intestinal infections are common (21–37 million diarrheal disease episodes in 16.5 million US children each year) and death can occur (around 200 annually in US and Canada). Necrotizing enterocolitis, for example, is one of the most devastating diseases that a preterm infant faces during its efforts to continue its fragile existence within a neonatal intensive care unit (NICU). The incidence of necrotizing enterocolitis, ranges from 10–25% of preterm infants (about 1,500 g in weight) admitted to the NICU, and may involve approximately one third to one half of all very low birth weight infants. Of those, approximately half will require surgery. The mortality ranges from 25–30%, and of those who survive, around 25% experience long term sequelae. In some cases, the sequelae result from multi-system organ failure which has damaged the lungs or other organs.

The infecting organisms are broad in their range, and include Clostridium, Escherichia, Klebsiella, Salmonella, Shigella, Campylobacter, Pseudomonas, Streptococcus, Enterococcus, Staphylococcus, coagulase-negative staphylococci, other Gram positive cocci, and other species including yeasts, viruses and protozoa.

A critical factor in protecting infants appears to be the formation of a protective intestinal flora. It is known that a flora high in protective bacteria (such as lactobacilli and bifidobacteria, believed to be transferred from the breast feeding mother), is critical to fighting off harmful organisms. However, the protective flora is not well established in these premature infants and by supplementing the flora with exogenous normal flora (either true probiotic organisms or the mother's own normal flora members) the risk of infection will be significantly reduced. Moreover, when infection ensues, treatment with probiotics will reduce the subsequent severity and longevity of the illness.

In recent years, Gregor Reid, Ph.D. and Andrew Bruce, M.D. have investigated the use of Lactobacillus to prevent and treat urogenital infections (Reid et al. (1998) *Int. Dairy J.* 8:555–562). This has included the development of probiotics which are ingested and which colonize and pass through the intestine to the vagina. These organisms have been shown to inhibit the growth and adhesion of pathogens and coaggregate to form a balanced normal flora which protects the host against infection.

The present invention now takes into account an infectious state not previously investigated for the application of probiotics, namely intestinal infections, particularly necrotizing enterocolitis, in premature newborn infants. While the importance of the ability of probiotic organisms to adhere and produce substances and conditions inhibitory to growth and adherence by harmful pathogens has been recognized, it has only now been appreciated, in accordance with the present invention that probiotics are primary colonizers i.e. the first microbes to reach the intestine and colonize the intestines of newborns.

The nature of the probiotic organisms which are used in this patient population is also important. These must adhere to intestinal cells, grow and survive and provide a health benefit to the host. Examples of appropriate strains are *Lactobacillus rhamnosus* GR-1, *Lactobacillus fermentum* RC-14 and Bifidobacterium. GR-1 and RC-14 have been demonstrated to produce substance antagonistic to various enteric pathogens (unpublished data and Velraeds et al. (1998) *J. Med. Microbiol.* 49:790–794). Bifidobacteria have been shown to effectively treat intestinal infections in Chernobyl patients in Russia, where the intestine has been damaged by exposure to radiation (unpublished data). There is also evidence to show that probiotics prevent and reduce the duration of diarrhea in older children whose intestinal flora has already been established. However, none of these studies have investigated newborns, nor addressed a situation where the newborn's intestine is undercolonized.

In studies of acute diarrhea (bacterial and rotaviral) in children 6 to 36 months of age, a *Lactobacillus reuteri* probiotic was given at 10e10 and 10e11 colony-forming units daily for 5 days and found to significantly reduce the duration of watery diarrhea compared with placebo (Shornikova et al. J. Pediatr. Gastroenterol. Nutr. 1997, 24: 399–404; and Shornikova et al. Pediatr. Infect. Dis. 1997, 16: 1103–1107). These studies described the safe application of probiotics to treat infection. The difference between these studies and the present invention is that the babies that are effectively treated by the present invention are premature, underweight newborns, who do not have a normal established flora, and the enterocolitis which they acquire is of a more serious nature to the child's survival.

SUMMARY OF THE INVENTION

The present invention demonstrates specially selected probiotic organisms with antagonistic properties against intestinal pathogens, can colonize, treat and provide protection against intestinal infection in newborns.

The present invention provides methods and compositions for the treatment and inhibition of intestinal infection caused by pathogenic organisms. Oral, rectal or intravenous administration of Lactobacillus and other probiotic compounds in a pharmaceutically acceptable carrier, such as milk or portions thereof provide a safe and effective means for colonizing the intestine, and treating, inhibiting or reducing the occurrence of intestinal infections in newborns.

In the practice of the compositions and methods of the present invention, the Lactobacillus may be administered as viable whole cells. The Lactobacillus species may be aerobically grown or microaerophillically grown and selected from *L. rhamnosus, L. acidophilus, L. crispatus, L. fermentum, L. plantarum, L. casei, L. paracasei, L. jensenii, L. gasseri, L. cellobiosis, L. brevis, L. delbrueckii, L. rogosae* and *L. bifidum*.

In one embodiment the present invention provides a newborn infant composition having one or more probiotic organisms such as lactobacillus and bifidobacteria.

In another embodiment of the present invention a newborn infant composition is provided having one or more probiotic organisms which are isolated from the intestinal flora of the newborn infant's mother.

In still another embodiment of the present invention a method is provided for colonizing the gastrointestinal flora in newborns comprising administering a therapeutically effective amount of at least one probiotic organism and a pharmaceutically acceptable carrier. In a further embodiment of the method a therapeutically effective amount of a second probiotic organism is administered. Lactobacillus is the preferred probiotic organism. Bifidobacteria is the preferred second probiotic organism. The Bifidobacterium is preferably selected from the group consisting of *B. bifidum, B. breve, B. adolescentis, B. infantis, B. pseudolongum, B. angulatum, B. catenulatum* or *B. longum*.

In yet another embodiment, the present invention describes a method of treating an infection in a newborn comprising administering a therapeutically effective amount of pharmaceutical composition comprising one or more isolated probiotic organisms and a pharmaceutically acceptable carrier to an infant in need of such treatment.

In still yet another embodiment, the present invention provides a method of enhancing protective gastrointestinal flora in newborns comprising administering a therapeutically effective amount of at least one probiotic organism and a pharmaceutically acceptable carrier.

DETAILED DESCRIPTION OF THE INVENTION

The present invention provides compositions and methods for the prevention and treatment of intestinal and other infections which originate from the intestine, in newborn infants by use of probiotic microbes or their by-products.

Premature infants weighing about 1500 g have little protective pioneer or primary-colonizing normal flora as a consequence of their neonatal low birth weight and underdeveloped intestinal epithelium. As a consequence, these newborns have an increased incidence of intestinal infections. In addition, premature infants typically receive antibiotic therapy and are prone to antibiotic-induced diarrhea, for example. Therefore, premature infants receive intravenous nutrition which disrupts or inhibits the formation of normal protective intestinal flora. The infections which ensue are commonly treated with antibiotics which further disrupt congenitally fragile flora.

While not wishing to be bound by a particular mechanism, the probiotic organisms of the present invention produce a primary barrier population which adheres to and protects the intestinal flora of the newborn and reduces the risk of infection and disease.

The ingestion or instillation of the probiotic organism compositions of the present invention enhances the protective flora and also enhances the recipient's immune system to fight off potential infecting microbes By "newborn" is meant an infant born at about 32 weeks, and weighing about 1500 g. By "probiotic" is meant an organism which has one or more of the following characteristics, an ability to:(i) adhere to cells; (ii) exclude or reduce pathogenic adherence; (iii) persist and multiply; (iv) produce acids, hydrogen peroxide and bacteriocin antagonistic to pathogen growth; (v) resist vaginal microbicides including spermicides; (vi) be safe and therefore noninvasive, noncarcinogenic and nonpathogenic; and (vii) coaggregate and form a normal, balanced flora.

A preferred probiotic bacteria is one or more species of lactobacillus and extracts or by-products thereof. The probiotic microbes are strains of lactobacilli and/or bifidobacteria conventionally derived from the mother of the newborn or an exogenous source. The probiotic microbes colonize the intestine, and have properties antagonistic to pathogens which cause enterocolitis. Pathogens antagonized or otherwise substantially eradicated by the probiotic compositions of the present invention are bacteria, protozoa, fungi and viruses which cause enterocolitis or related infections. The pathogens include but are not limited to Clostridium, Escherichia, Klebsiella, Salmonella, Shigella, Campylobacter, Pseudomonas, Streptococcus, Enterococcus, Staphylococcus, coagulase-negative staphylococci, other Gram positive cocci, and other species including yeasts, viruses and protozoa.

In another embodiment of the present invention the pathogen may be resistant to antibiotics, as is the case with multi-resistant staphylococcus aureus (MRSA) and vancomycin-resistant enterococci (VRE). In these situations, the probiotics of the present invention are administered to the newborn to treat the infection and to bind to the pathogens thereby reducing their infectivity. While not wishing to be bound by a particular mechanism, the probiotic organisms bind to and coaggregate with the pathogens thereby forming a biofilm. The biofilm functions to reduce the toxic effects of the pathogens to the host, thereby inhibiting or preventing the infectious process.

The invention utilizes therapeutically effective amounts of one or more of the probiotic organisms, and/or their metabolic by-products, within days, and preferably within about 72 hours, of the birth of the newborn. The composition is instilled orally or rectally in the form of freeze dried preparation, paste, liquid, gel or other delivery mechanism including a rectal suppository. The probiotic organisms may also be administered intravenously, parenterally or intraperitoneally. Dispersions can also be prepared, for example, in glycerol, liquid polyethylene glycols, and mixtures thereof, and in oils.

The probiotic bacteria of the present invention are used to counteract bacteria and viruses in the intestinal tracts. Other orifices and surfaces are colonized naturally by organisms without any known detrimental affect to the host. These include the nasopharynx and skin. In accordance with the present invention probiotic agents are applied to sites, such as the nasopharynx and skin. In these cases, the probiotic organisms of choice may not be lactobacilli or bifidobacteria, but may be other aerobes or anaerobes.

In another embodiment the composition is applied in suspension, as a topical application to orifaces, such as wounds, the oral cavity and nasopharynx of a newborn. Administration to the oral cavity is by mouth or by application of a medical device (inserted into the infants' mouth) onto which viable or non-viable organisms or their by-products are coated.

By "therapeutically effective amount" as used herein is meant an amount high enough to significantly positively modify the condition to be treated but low enough to avoid serious side effects (at reasonable benefit/risk ratio) within the scope of sound medical judgment. The therapeutically effective amount will vary with the particular condition being treated, or the condition of the newborn and his/her physical condition, as well as the type of preparation being used.

In the practice of the method as hereinabove defined, the probiotic bacteria may be administered as viable whole cells. The Lactobacillus may be aerobically, anaerobically or microaerophilically grown, preferably selected from the group consisting of *L. casei, L. rhamnosus, L. acidophilus, L. plantarum, L. fermentum, L. reuteri, L. jensenii, L. gasseri, L. cellobiosus, L. crispatus, L. brevis, L. salivarius, L. paracasei, L. delbrueckii, L. helveticus, L. collinoides, L. buchneri, L. rogosae,* and *L. bifidum*.

In a preferred aspect, the Lactobacillus is selected from the group consisting of *Lactobacillus casei var rhamnosus* (GR-1 (ATCC 55826), *L. casei var rhamnosus* GR-2 (ATCC 55915), *L. casei var rhamnosus* GR-3 (ATCC 55917), *L. casei var rhamnosus* GR-4 (ATCC 55916), *L. casei var rhamnosus* RC-9, *L. casei var rhamnosus* RC-17 (ATCC 55825), *L. casei var alactosus* RC-21, *L. casei* NRC 430, *L. casei* ATCC 7469, *L. casei var rhamnosus* 81, *L. casei var rhamnosus* 76, *L. casei var rhamnosus* 36 W, *L. casei var rhamnosus* 36 g, *L. casei* RC-65, *L. casei* RC-15, *L. casei* 558, *L. casei,* RC-21, *L. casei* 55, *L. casei* 8, *L. casei* 43, *L. plantarum* RC-12 (ATCC 55895), *L. acidophilus* RC-25, *L. plantarum* RC-19, *L. jensenii* RC-11 (ATCC 55901), *L. acidophilus* ATCC 4357, *L. acidophilus* 2099 B, *L. acidophilus* 2155 C, *L. acidophilus* T-13, *L. acidophilus* 1807B, *L. acidophilus* RC-16, *L. acidophilus* RC-26, *L. acidophilus* RC-10, *L. acidophilus* RC-24, *L. acidophilus* RC-13, *L. acidophilus* RC-14, *L. acidophilus* RC-12, *L. acidophilus* RC-22, *L. acidophilus* 2099B, *L. acidophilus* 2155C, *L. acidophilus* T-13, *L. plantarum* ATCC 8014, *L. plantarum* UH 2153, *L. plantarum* 260, *L. plantarum* RC-20, *L. plantarum* 75, *L. plantarum* RC-6, *L. fermentum* A-60, *L. fermentum* B-54 (identical ribotype to RC-14) (ATCC 55920), *L. cellobiosis* RC-2, *L. crispatus* 1350B and *L. crispatus* 2142B. A most preferred lactobacillus species is *L. fermentum* RC-14. Another preferred lactobacillus species is *L. rhamnosus* GR-1. Still another preferred lactobacillus species is *L. ferrmentum* B-54.

The bifidobacteria may be anaerobically grown and preferably selected from the group consisting of *Bifidobacterium adolescentis, B. bifidum, B. infantis, B. pseudolongum, B. angulatum, B. catenulatum* or *B. longum*.

The bifidobacteria and/or lactobacilli are isolated from the newborn mother's intestine via a fecal sample, then purified, grown anaerobically and reimplanted into the newborn together with a pharmaceutically acceptable carrier. It has been found in accordance with the present invention that a composition comprising about $10^3$/ml to about $10^9$/ml probiotic organisms is suitable for treating and preventing intestinal infections and/or enhancing protective flora in newborns.

By "pharmaceutically-acceptable carrier" as used herein is meant one or more compatible solid or liquid filler diluents, or encapsulating substances. By "compatible" as used herein is meant that the components of the composition are capable of being comingled without interacting in a manner which would substantially decrease the pharmaceutical efficacy of the total composition under ordinary use situations.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations. Wetting agents and lubricants such as sodium lauryl sulfate, as well as coloring agents, flavoring agents, lubricants, excipients, tabletting agents, stabilizers, anti-oxidants and preservatives, can also be present.

The pharmaceutically acceptable carrier may be in the form of milk or portions thereof including yogurt. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized.

The invention will now be illustrated by means of the following non-limiting examples.

EXAMPLE 1

As soon as the baby is born, and is found to be premature or about 1,500 g in weight, and once it is in a stable enough condition to receive fluids by mouth, a probiotic composition is administered once or more times (up to about five) daily for between 1 and about 140 to about 168 days (six months). The probiotics are preferably contained in a saline or milk suspension, if milk then preferably that of the mother's, in numbers approximately >1,000 per ml to 100,000,000 per ml. It is expected that 1 ml will be administered each time, but this will depend upon the estimated benefit/risk situation decided by the neonatologist. The ideal dosage will be sufficient to allow the probiotic organisms to colonize the newborn's intestine. The duration of treatment will extend for the duration of the child's stay in the NICU, or the time at which it is most susceptible to enterocolitis. One example of a dosage would be 1 ml of a concentration of 100,000,000 per ml five times daily for one week to establish the organisms in the gut, then a maintenance dose of up to about 5 ml at 1,000,000 per ml once daily for the remainder of stay in NICU or, if discharged but still susceptible to infection, for a further three months.

EXAMPLE 2

The second situation for application of the probiotics would be a newborn who has left the hospital, but who is deemed to be at risk of infections, perhaps through immunosuppression, or other ailments, or who has had antibiotic therapy and their normal gut flora has been disrupted. The probiotic composition is taken once daily (with or without the antibiotics) for periods ranging from days to months, depending upon the degree of susceptibility to infection.

EXAMPLE 3

Probiotic strains originating from the mother are utilized where it is recognized that newborn delivery is likely. A fecal sample is collected from the mother, and the most dominant lactobacilli and bifidobacteria present in the stool are isolated, purified and grown to sufficient numbers to allow implantation into the newborn. The organisms are suspended in either skim milk, or the mother's milk if available, then implanted as in examples 1 and 2. The strains are speciated and stored in glycerol vials in the freezer or as freeze dried vials.

EXAMPLE 4

If enterocolitis signs and symptoms appear or an intestinal infection is suspected by a physician, or laboratory diagnosis confirms infection is present, probiotics compositions are administered to the infant by oral or rectal delivery. This will occur more than once per day, especially if the child is vomiting and has diarrhea, (thereby making it difficult for administered probiotics to stay in the stomach or intestine long enough for them to colonize).

EXAMPLE 5

The probiotics herein described are administered in combination with antibiotics given to eradicate the offending pathogens in the gut, or given for other purposes (e.g. for secondary lung infection). In this example, the probiotic organisms selected for such usage, are resistant to the antibiotics being administered. This combination treatment permits the normal barrier population of the intestine to be strengthened at the same time that the harmful bacterial count is depleted.

EXAMPLE 6

Bifidobacteria and/or lactobacilli are isolated from the newborn mother's intestine via a fecal sample as follows. A fecal sample is dispersed in saline and a sample is diluted and plated onto agar which supports the preferred growth of the desired organisms, such as MRS agar or Rogosa's agar. Colonies of the most dominant lactobacilli or bifidobacteria then grow, and they are purified and conventionally tested by Gram stain and biochemical and molecular typing methods to confirm their purity and speciation. The bacterium is then grown to produce large numbers, in a broth culture for two days under anaerobic conditions. The organisms are washed to remove excess broth, then stored in a freeze dried form or in glycerol stock cultures in the −70° C. freezer. Prior to re-inoculating into the newborn, the organisms are subcultured in broth, grown, washed and resuspended in suitable concentrations and a pharmaceutically acceptable carrier (such as skim milk or saline) then administered to the newborn.

What is claimed is:

1. A method of colonizing gastrointestinal flora in newborns comprising administering a therapeutically effective amount of at least one probiotic organism selected from the group consisting *Lactobacillus rhamnosus* GR-1 and *Lactobacillus fermentum* RC-14 and a pharmaceutically acceptable carrier.

2. The method of claim 1 further comprising the administration of a therapeutically effective amount of at least one second probiotic organism.

3. The method of claim 2 wherein said second probiotic organism is a Bifidobacterium.

4. The method of claim 2 wherein said second probiotic organism is selected from the group consisting of *B. bifidum, B. adolescentis, B. infantis, B. pseudolongum, B. angulatum, B. catenulatum* and *B. longum*.

5. A method of enhancing protective gastrointestinal flora in newborns comprising administering a therapeutically effective amount of at least one probiotic organism selected from the group consisting *Lactobacillus rhamnosus* GR-1 and *Lactobacillus fermentum* RC-14 and a pharmaceutically acceptable carrier.

* * * * *